US010543266B2

(12) United States Patent
Ella et al.

(10) Patent No.: US 10,543,266 B2
(45) Date of Patent: Jan. 28, 2020

(54) POLYSACCHARIDE VACCINE FORMULATIONS AND PROCESSES FOR INDUSTRIAL PRODUCTION OF BACTERIAL POLYSACCHARIDES

(71) Applicant: BHARAT BIOTECH INTERNATIONAL LIMITED, Hyderabad (IN)

(72) Inventors: Krishna Murthy Ella, Hyderabad (IN); Ashawani Kumar, Hyderabad (IN); Venkatesan Ramaswamy, Hyderabad (IN); Voleti Subrahmanya Ramachandra Murthy, Hyderabad (IN)

(73) Assignee: Bharat Biotech International Ltd., Hyderabad (IN)

( * ) Notice: Subject to any disclaimer, the term of this patent is extended or adjusted under 35 U.S.C. 154(b) by 0 days.

(21) Appl. No.: 15/741,669

(22) PCT Filed: Jul. 4, 2016

(86) PCT No.: PCT/IN2016/050218
§ 371 (c)(1),
(2) Date: Jan. 3, 2018

(87) PCT Pub. No.: WO2017/006349
PCT Pub. Date: Jan. 12, 2017

(65) Prior Publication Data
US 2018/0185465 A1 Jul. 5, 2018

(30) Foreign Application Priority Data
Jul. 4, 2015 (IN) ........................... 3426/CHE/2015

(51) Int. Cl.

| | |
|---|---|
| ***A61K 39/095*** | (2006.01) |
| ***A61K 47/64*** | (2017.01) |
| ***A61K 39/00*** | (2006.01) |
| ***A61K 39/116*** | (2006.01) |
| ***A61K 39/112*** | (2006.01) |
| ***A61P 31/04*** | (2006.01) |
| ***A61K 47/24*** | (2006.01) |
| ***C12N 1/20*** | (2006.01) |
| ***C12P 19/04*** | (2006.01) |

(52) U.S. Cl.
CPC ........ *A61K 39/095* (2013.01); *A61K 39/0275* (2013.01); *A61K 47/24* (2013.01); *A61P 31/04* (2018.01); *C12N 1/20* (2013.01); *C12P 19/04* (2013.01); *A61K 39/116* (2013.01); *A61K 47/646* (2017.08); *A61K 2039/6037* (2013.01); *A61K 2039/6087* (2013.01); *A61K 2039/70* (2013.01); *Y02A 50/482* (2018.01); *Y02A 50/484* (2018.01)

(58) Field of Classification Search
CPC combination set(s) only.
See application file for complete search history.

(56) References Cited

U.S. PATENT DOCUMENTS

| | | | |
|---|---|---|---|
| 8,129,147 | B2 | 3/2012 | Reddy et al. |
| 2014/0377302 | A1 | 12/2014 | Vinayak et al. |

FOREIGN PATENT DOCUMENTS

| | | |
|---|---|---|
| WO | WO2014009971 | 1/2014 |
| WO | WO2014080423 | 5/2014 |

OTHER PUBLICATIONS

Jones et al., "Endotoxin, Capsule, and Bacterial Attachment Contribute to Neisseria meningitidis Resistance to the Human Antimicrobial Peptide LL-37" Journal of Bacteriology, vol. 191, No. 12, pp. 3861-3868, (Jun. 2009). p. 3864, table 1.
Examination Report for IN Application No. 201747045063 dated Jun. 20, 2018.
Search and Examination Report for EP Application No. 16820976.5 dated Dec. 12, 2018.
Search Report for International Application No. PCT/IN2016/50218 dated Dec. 13, 2016.
Patentability Report for International Application No. PCT/IN2016/50218 dated Jan. 9, 2018.

*Primary Examiner* — Sarvamangala Devi
(74) *Attorney, Agent, or Firm* — Remenick PLLC

(57) ABSTRACT

The present invention relates to the field of combined vaccine compositions which are effective against all forms of meningococcal diseases as well as typhoid fever. The vaccine formulations comprising antigens from capsular polysaccharides of *Neisseria meningitidis* A, *Neisseria meningitidis* C, *Neisseria meningitidis* Y, *Neisseria meningitidis* W135, *Neisseria meningitidis* X, *Salmonella typhi* Vi capsular polysaccharide (ViPs) or capsular ViPs conjugated to a carrier protein tetanus toxoid (ViPs-TT). This invention is also related to improved methods, especially the use of an improved feed media and an improved method of downstream processing and industrial purification of capsular polysaccharides. The vaccine is free of any animal component or alcohol and is in absolute compliance with respect to the religious sentiments of various ethnic groups. The composition is highly effective and stable, yet cost-effective and affordable, especially for lower-middle income and low-income countries.

20 Claims, 15 Drawing Sheets

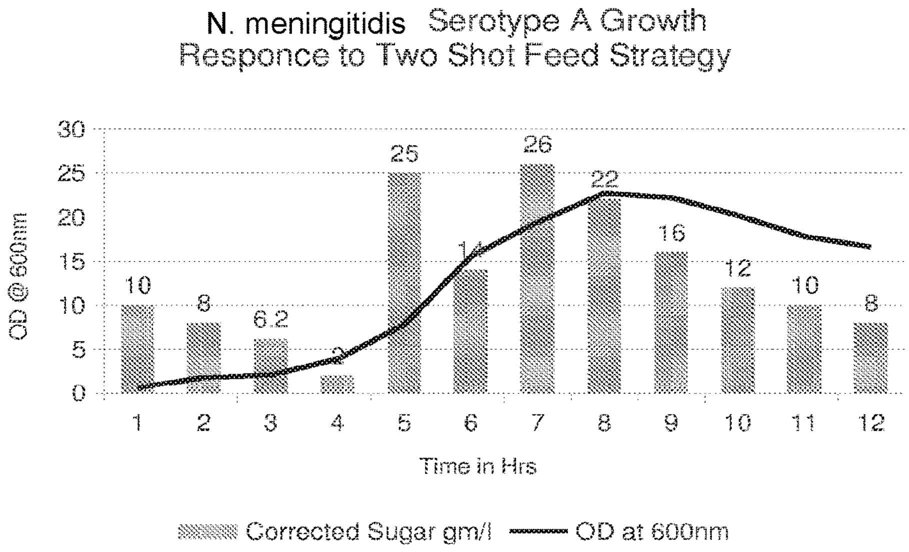
Fig-1 Growth Kinetics of *N. meningitidis* serotype A 200L fermentation batch taken with two Shot feeding strategy.

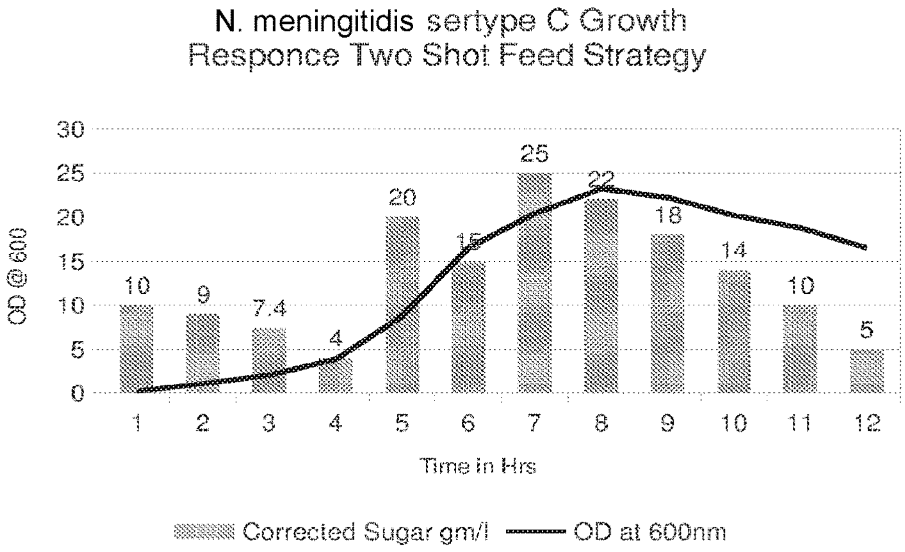
Fig-2 Growth Kinetics of *N. meningitidis* serotype C 200L fermentation batch taken with two Shot feeding strategy.

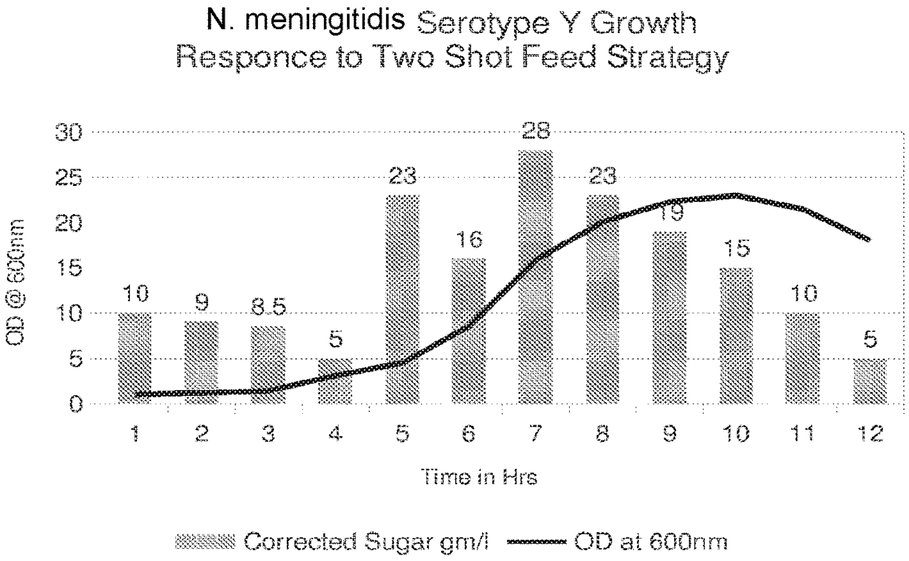
Fig-3 Growth Kinetics of *N. meningitidis* serotype Y 200L fermentation batch taken with two Shot feeding strategy.

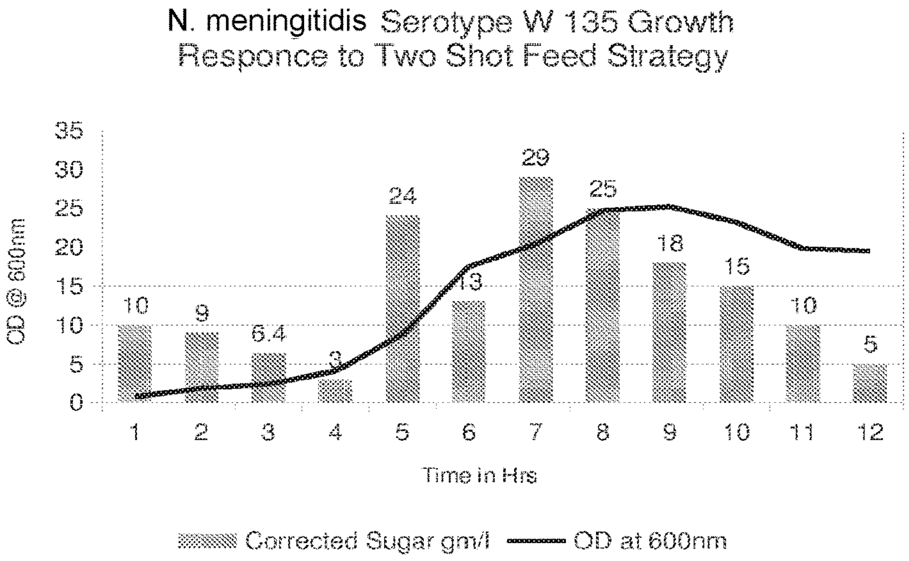
Fig-4 Growth Kinetics of *N. meningitidis* serotype W135 200L fermentation batch taken with two Shot feeding strategy.

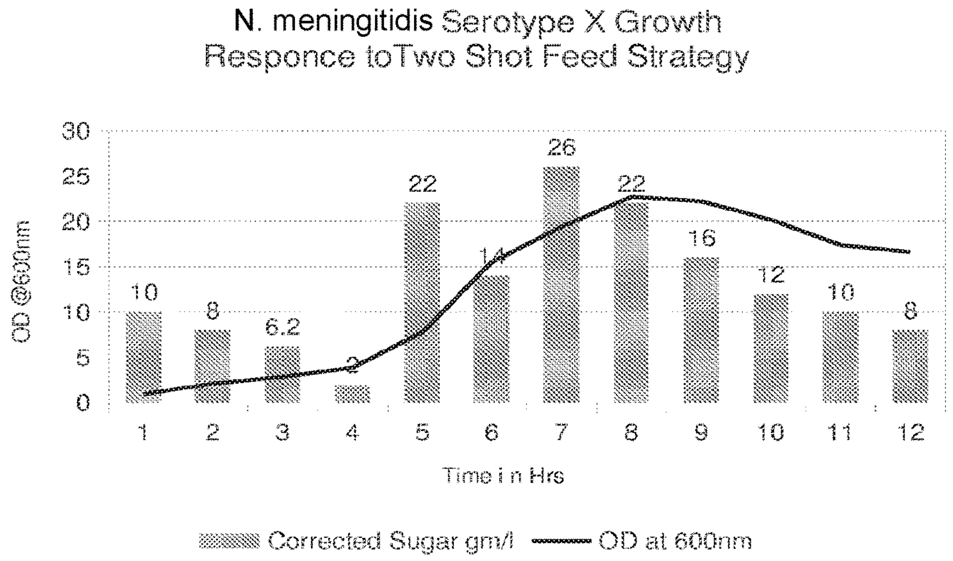
Fig-5 Growth Kinetics of *N. meningitidis* serotype X 200L fermentation batch taken with two Shot feeding strategy.

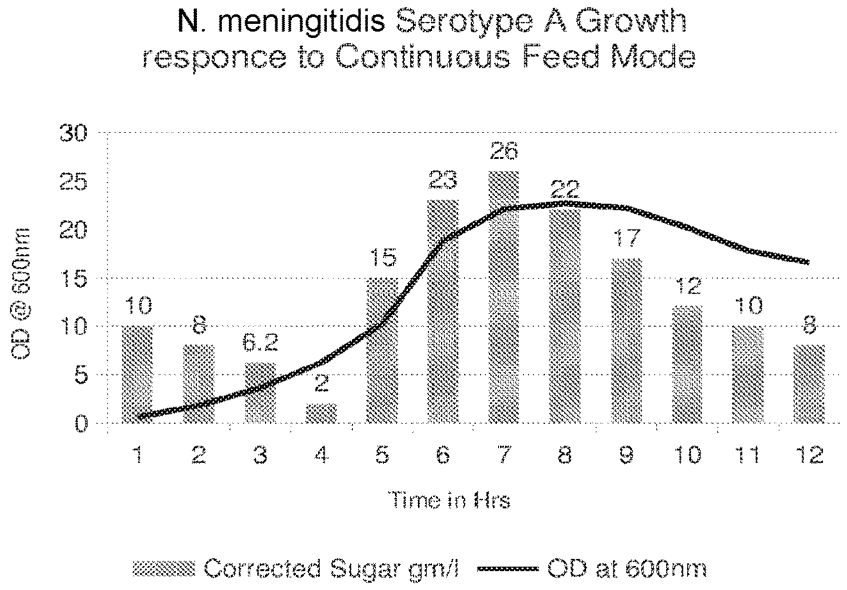
Fig-6 Growth Kinetics of *N. meningitidis* serotype A 200L fermentation batch taken with continuous feeding Mode.

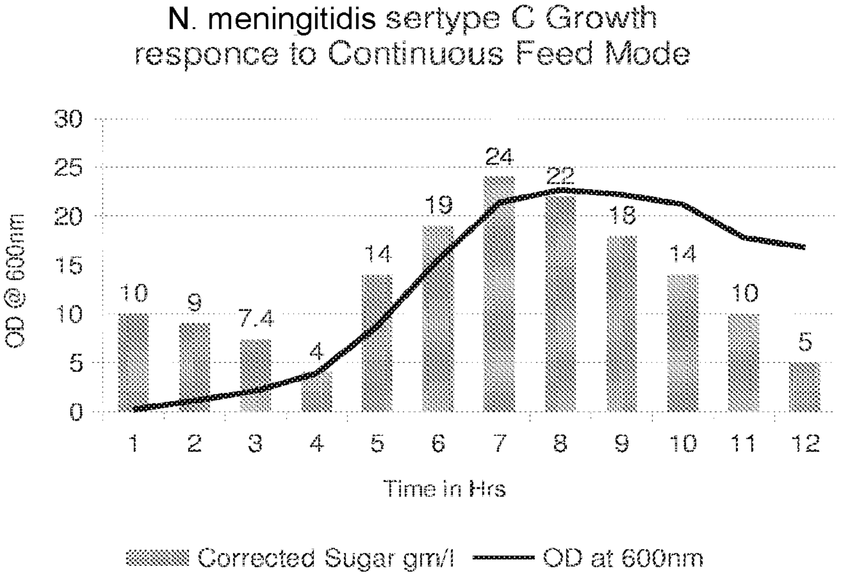
Fig-7 Growth Kinetics of *N. meningitidis* serotype C 200L fermentation batch taken with continuous feeding Mode.

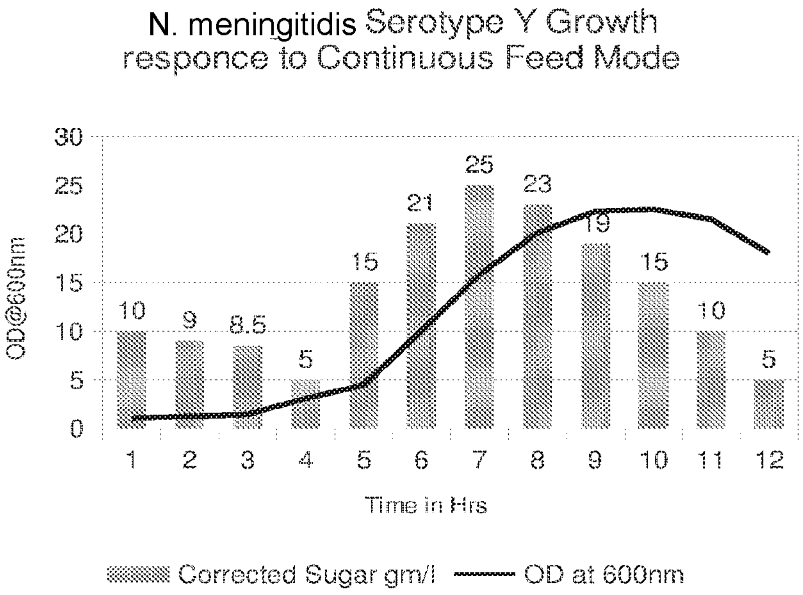
Fig-8 Growth Kinetics of *N. meningitidis* serotype Y 200L fermentation batch taken with continuous feeding mode.

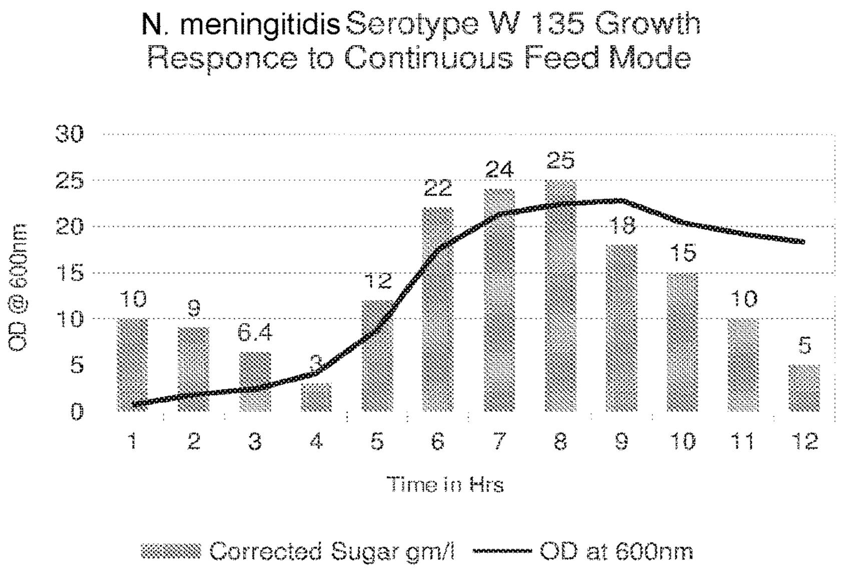
Fig-9 Growth Kinetics of *N. meningitidis* serotype W135 200L fermentation batch taken with continuous feeding mode.

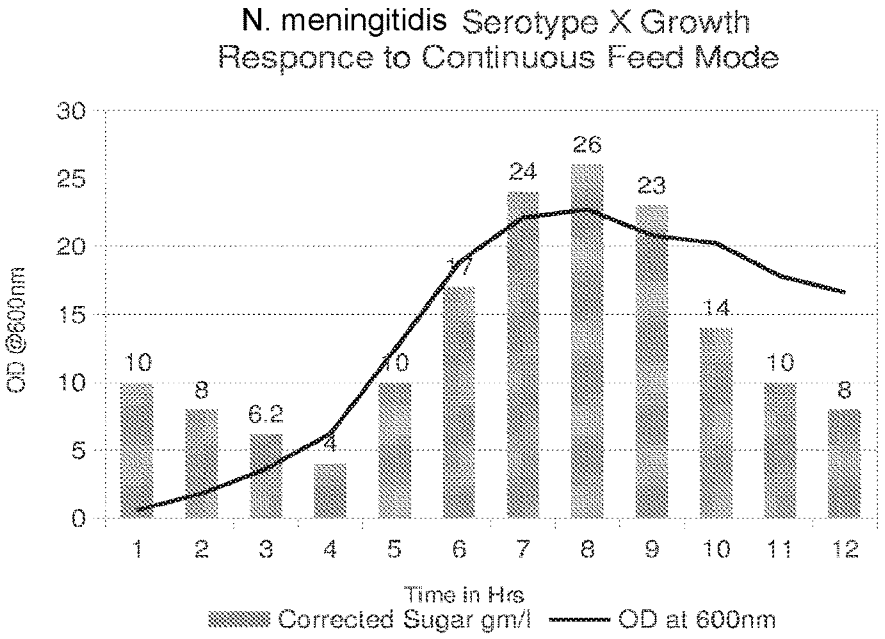
Fig-10 Growth Kinetics of *N. meningitidis* serotype X 200L fermentation batch taken with continuous feeding Mode.

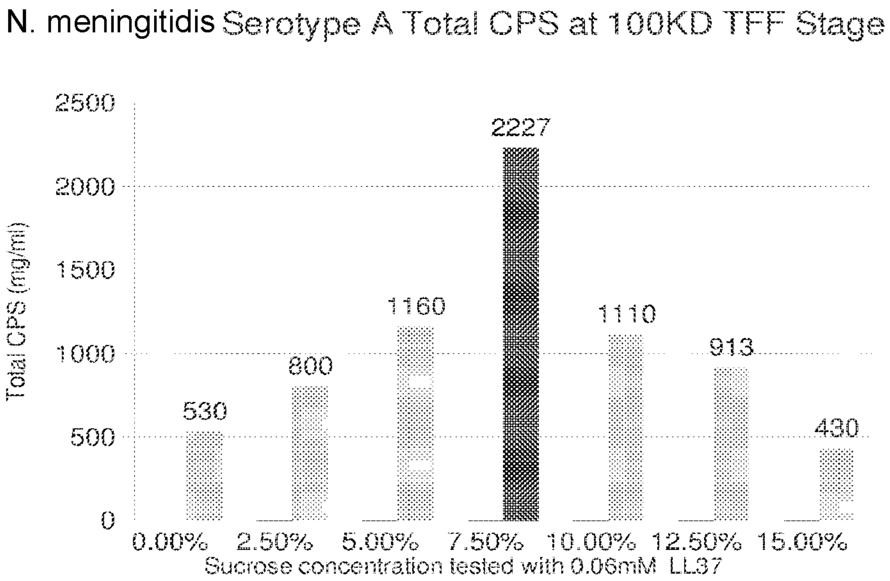
Fig- 11 Total CPS concentration of N. meningitidis Serogroup A at 100kd stage

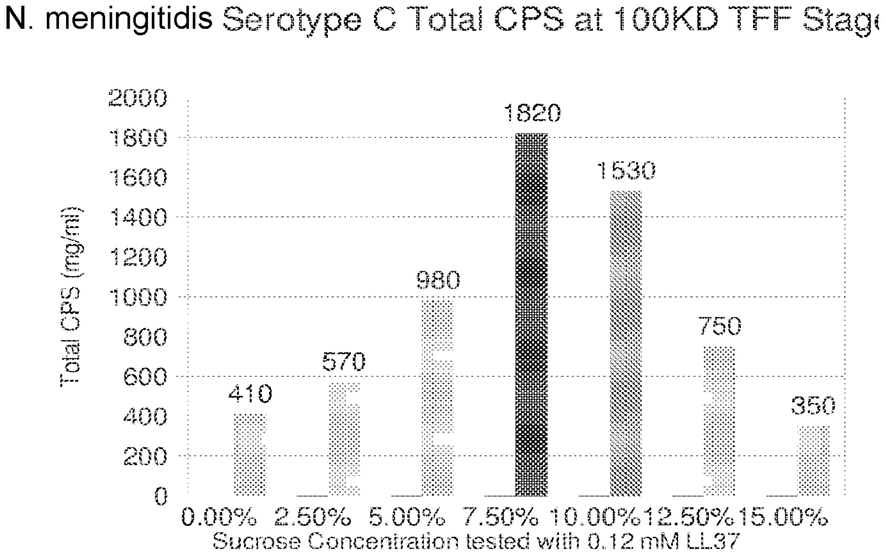
Fig-12 Total CPS concentration of N. meningitidis Serogroup C at 100kd stage

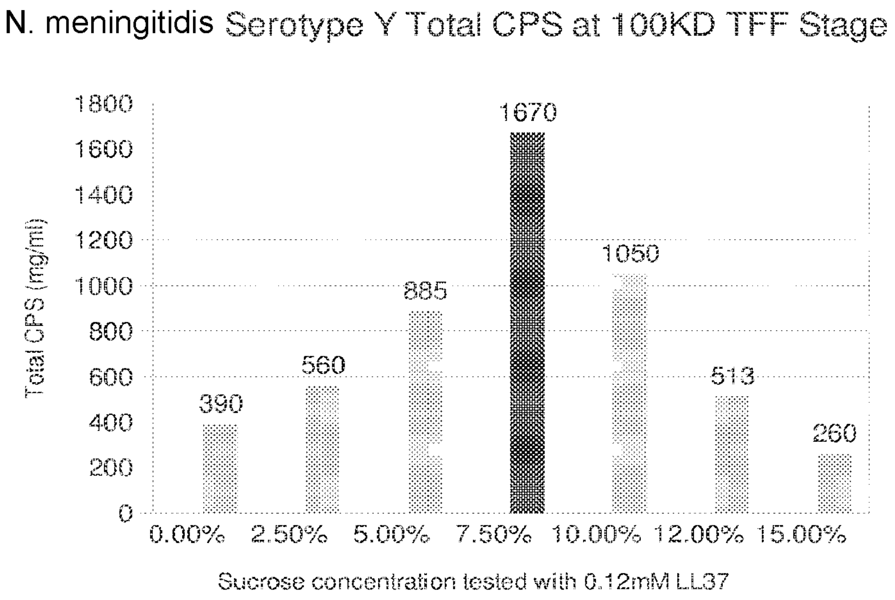
Fig-13 Total CPS concentration of N. meningitidis Serogroup Y at 100kd stage

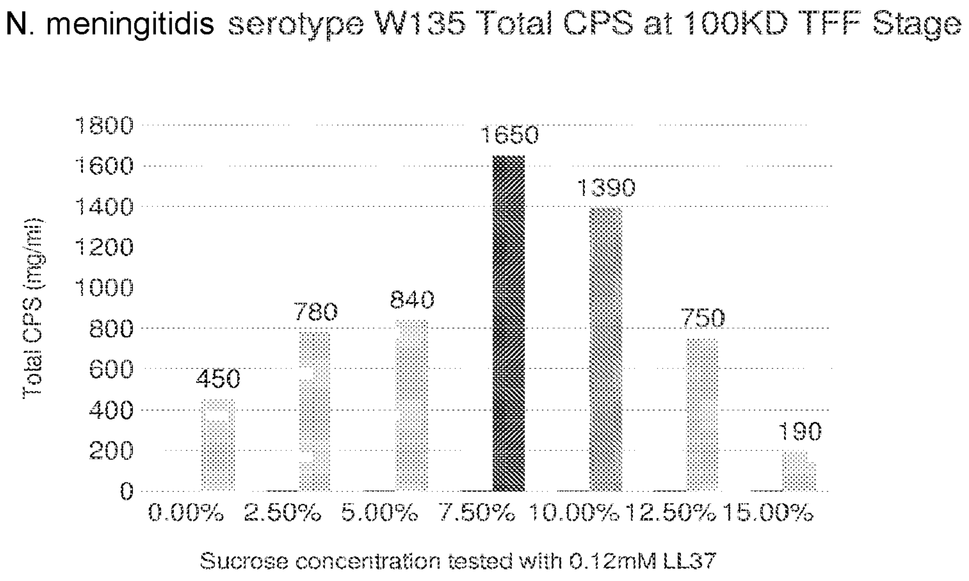
Fig-14 Total CPS concentration of N. meningitidis Serogroup W135 at 100kd stage

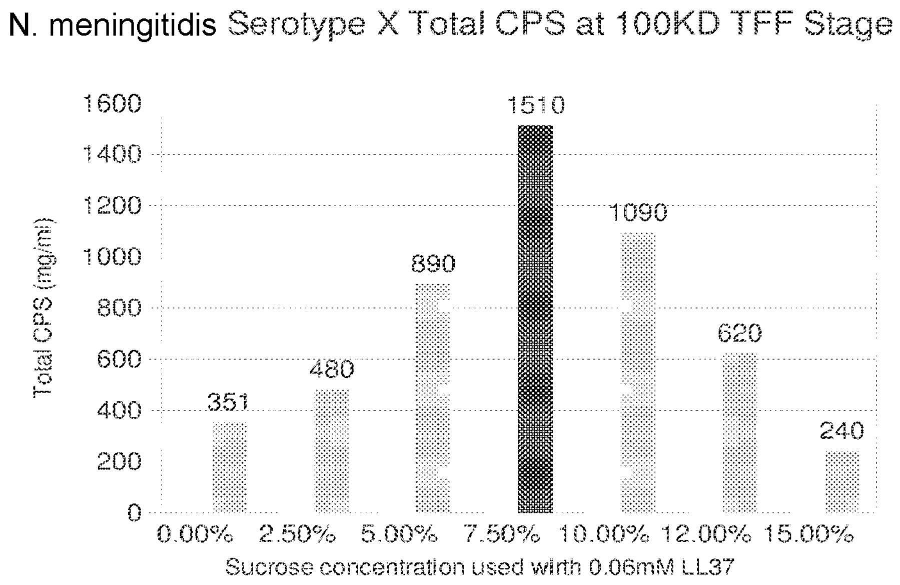
Fig-15 Total CPS concentration of N. meningitidis Serogroup X at 100kd stage
N. meningitidis Serotype X Total CPS at 100KD TFF Stage
| Sucrose concentration used with 0.06mM LL37 | Total CPS (mg/ml) |
|---|---|
| 0.00% | 351 |
| 2.50% | 480 |
| 5.00% | 890 |
| 7.50% | 1510 |
| 10.00% | 1090 |
| 12.00% | 620 |
| 15.00% | 240 |

POLYSACCHARIDE VACCINE FORMULATIONS AND PROCESSES FOR INDUSTRIAL PRODUCTION OF BACTERIAL POLYSACCHARIDES

This application is a U.S. national phase application under 35 U.S.C. of § 371 of International Application No. PCT/IN2016/050218, filed Jul. 4, 2016, which claims priority of Indian Patent Application No. 3426/CHE/2015, filed Jul. 4, 2015, the disclosure of which is hereby incorporated by reference herein.

FIELD OF INVENTION

This invention pertains to the field of polysaccharide vaccines. More particularly, this invention relates to the field of process for preparation and manufacture of combined polysaccharide vaccines. The invention also relates to the industrial production and cultivation of bacterial polysaccharides associated in vaccine production and formulations. Furthermore, this invention also relates to the field of combined vaccine formulations, wherein the said combination vaccine is effective against certain endemic infections, comprising respective bacterial polysaccharide as vaccine antigens in combination of different serotypes of *Neisseria meningitidis* and *Salmonella typhi* Vi polysaccharide conjugate antigens. This invention is related to deliver improved methodologies in the field of vaccine production, especially in the domain of capsular polysaccharide vaccine formulations.

BACKGROUND OF THE INVENTION

Meningococcal meningitis is the disease identified as the inflammation of meningitis of brain and spinal cord. The causing agent behind bacterial meningitis is *Neisseria meningitidis*. Clinical manifestation of meningococcal infection includes fever, headache, photophobia, neck stiffness, occasional seizures, altered mental status, nausea, vomiting, myalgia, and petechial or purpuric rash (28-77%). Despite antibiotic therapy the mortality rate is higher and sometimes consequences are permanent. After sequel consequences may include loss of hearing, diminished vision or loss of limb due to gangrene formation. *Neisseria meningitidis* are the gram-negative diplococci which were identified on the basis of their capsular polysaccharides. So far 12 antigenic distinct capsular groups has been identified according to characteristics of the polysaccharide capsule for this microorganism, which include *Neisseria meningitidis* A, *Neisseria meningitidis* B, *Neisseria meningitidis* C, *Neisseria meningitidis* E, *Neisseria meningitidis* H, *Neisseria meningitidis* I, *Neisseria meningitidis* K, *Neisseria meningitidis* L, *Neisseria meningitidis* W135, *Neisseria meningitidis* X. *Neisseria meningitidis* Y, and *Neisseria meningitidis* Z. They can be further distinguished to various types and sub type based on the outer membrane proteins. They are also identified as various sequence type (ST) based on the sequencing of certain regions of their chromosomal DNA. Out of 12, six capsule types (*Neisseria meningitidis* A, *Neisseria meningitidis* B, *Neisseria meningitidis* C, *Neisseria meningitidis* Y, *Neisseria meningitidis* W135 and *Neisseria meningitidis* X) were found responsible for the invasive meningitis and septicemia world wide. The relative importance of each serogroups varies with geographic region. Therefore, determining serogroup responsible for the sporadic case is important for containment of disease in a particular geographical location. The cause of disease development in some carriers is not completely understood. However, few identified risk factors are age, season, smoking, preceding influenza A infection and living in 'closed' or 'semi-closed' communities (Cartwright, 1995). Meningococcal infection establishes harmless commensal relationship colonizing the nasopharynx among 25% adolescents and 5 to 11% of human adults without any symptoms of illness. But in the case of infection among infants and young children, the carriage rate is low as compared to adults (Christensen et al., 2010). The mode of meningococcal transmission is by aerosol, droplets or direct contact with respiratory secretions of someone carrying the organism. Transmission usually requires either frequent or prolonged close contact like exposure to the bacteria. There is a marked seasonal variation in meningococcal disease, with peak levels in the winter months declining to low levels by late summer.

Meningococcal meningitis is a major public health problem in many countries. As per the WHO estimates world wide annual burden of meningococcal disease is approximately 300,000 to 350,000 cases. The incidence is much higher in many developing countries (about 25/100,000) compared to the US or Western Europe (1-4/100,000). Serogroup A was the cause of most meningococcal disease in the earlier 20th century and is now responsible for recurring epidemics in developing countries, particularly in sub-Saharan Africa. From 2000 to 2002, epidemics of serogroup W-135 occurred, related to spread during the hajj pilgrimage, affecting the health of these travelers and their contacts in countries throughout the world. Serogroup B is the most important cause of endemic disease in developed countries (30-40%) and 80% of disease in the United States and European countries, respectively), and serogroup C has variable rates of endemic occurrence (currently around 30%) in industrialized countries (Jackson et al., 1995). Serogroup Y has emerged in the last decade in the United States and caused one-third of the disease related to meningococcal infections in the country (Rosenstein et al., 1999), usually affecting older age groups. Interestingly, meningococcal pneumonia is usually due to serogroups Y and W-135. Serogroup X has recently been found associated with increase in meningococcal disease outbreak in African meningitidis belt. The outbreaks were reported from Niger, burkina Faso, Tongo and Ghana. In 2010 over 6500 meningitidis cases were reported alone in Burkina Faso out of which 1000 cases were found associated with Serogroup X. Again in 2011 out of 3155 cases of meningitidis, 60% were linked to the Meningitidis X serotype.

Hence, based on the varied epidemiology of the disease a number of commercial vaccines has been made available till date based on the region of occurrence of specific serotypes of *Neisseria meningitidis*.

TABLE 1

Commercial Meningococcal Vaccines available in the market

| Sr. No. | Tradename | Name of manufacturer | Type of Vaccine | Serogroups Covered | Countries where licensed |
|---|---|---|---|---|---|
| 1 | Bexsero ® | GSK | Recombinant | B | USA, Europe, Australia |
| 2 | Menactra ® | Sanofi Pasteur | Conjugate | A, C, Y, W135 | USA, Canada, India, Australia, Arab and Gulf countries |
| 3 | MenHibrix ® | GSK | Conjugate | C, Y and *Haemophilus influenzae* type b PRP | USA |
| 4 | Menitorix ® | GSK | Conjugate | C | Europe, Australia |
| 5 | Menomune ® | Sanofi Pasteur | Polysaccharide | A, C, W135, Y | USA |
| 6 | Menveo ® (MCV4 type) | Novartis | Conjugate | A, C, W135, Y | USA, Canada, Europe, and Australia |
| 7 | Trumenba ® | Pfizer | Recombinant | B | USA, Europe, Australia, Canada |
| 8 | MenAfriVac ® | Serum Institute of India | Conjugate (Lyophilized) | A | India and Africa |
| 9 | Mencevax ® | Pfizer | Polysaccharide (Lyophilized) | A | Approved in 79 countries across Africa, Asia, Australia, Europe, Latin America, Middle East and New Zealand. |
| 10 | NmVac4-A/C/Y/W-135 ® | J.N International Medical Corporation | Conjugate | A, C, W135, Y | Gulf Countries |
| 11 | Nimenrix ® | Pfizer Canada | Conjugate | A, C, W135, Y | Approved for sale in more than 61 countries including the European Economic Area, Canada and Australia |
| 12 | VA-MENGOC-BC ® | Finlay Institute | Outer Membrane Vesicle Protein | B | Cuba, Brazil, El Salvador, Nicaragua, the Dominican Republic, Colombia, Argentina and Syria |
| 13 | MeNZB ™ | Chiron | Outer Membrane Vesicle Protein | A specific strain of serogroup B | Only in Newzealand (Immunization Program ended in 2011 and vaccine is not available in Newzealand anymore) |

Thus we see that, a majority of the vaccine available against Meningococcal meningitis is available only in the developed nations in the Western World, and very few are available in the developing nations, or low or middle economy countries. However, epidemiological studies report that Africa includes at least 25 countries having the highest annual incidence of meningococcal disease in the world. Majority of the diseases are caused by serogroup A meningococcal infection, though it has been reported that serogroups C, W-135 and X are also prevalent. It has been reported that the rate of meningococcal diseases can be as high as 224 incidences/100,000 population in this belt. The South American nations has also shown high rate of prevalence of serogroups B and C (Jafri, R., Ali, A., Messonnier, N., Tevi-Benissan, C., Durrheim, D., Eskola, J., Fermon, F., Klugman, K., Ramsay, M., Sow, S., Zhujun, S., Bhutta, Z. and Abramson, J. (2013). Global epidemiology of invasive meningococcal disease. *Popul Health Metrics,* 11(1), p. 17.). In the Eastern Mediterranean region, the predominant serogroups are A and W-135. Countries like Sudan and Saudi Arabia in the Eastern Mediterranean are the main sufferers. In most of the Asian countries, few studies have shown that the burden of the diseases in these developing countries may be significant. Apart from the prevalent serogroup A, diseases resulting from serogroups C, Y and W-135 have been reported. There have been meningococcal epidemics in many countries like Cambodia, China, Hong Kong, Indonesia, Malaysia, etc. India has also experienced repeated meningococcal serogroup A epidemics over the last 2 to 3 decades. (VYSE, A., WOLTER, J., CHEN, J., NG, T. and SORIANO-GABARRO, M. (2011). Meningococcal disease in Asia: an under-recognized public health burden. *Epidemiol. Infect.,* 139(07), pp. 967-985.)

Hence, it is established that Meningococcal infections are not only restricted to occurrence in developed nations such as in US, Canada and Europe or Australia. However, there has been a lacuna in developing cost-effective meningococcal vaccines in those neglected areas of the World like African and Asian countries despite occurrence of varied meningococcal infections. Further, the individual vaccines available so far do not offer complete protection against all the serotypes in a specific region. There are still possibilities of varied Meningococcal infections within a given region, wherein the vaccines against particular serotype are not available at all. A particular subject vaccinated with a single or either two or three serotypes of the vaccine is still not completely protected against any potential infection due to a meningitidis serotype, which he or she has not been vaccinated with. Therefore, there is a necessity to develop more cost-effective meningitis vaccines which will offer prophylaxis against varied serotypes in a single combination vaccine against all meningitis serotypes irrespective of the nature of meningococcal infection. HAJJ pilgrims comprising the Muslim population from all over the World converge at Mecca every year. This increases the possibilities to contract varied meningitis infection by the Hajj pilgrims as the possibility of getting infected increases due to scarcity of hygienic food and water including sanitary considerations. It has been reported that at least 225 cases of meningococcal diseases are recorded each year after the Hajj season in Saudi Arabia due to the conglomeration of a large number of people from all over the world. Absence of potable drinking water also contributes to the risk of getting infected of typhoid fever due to infection by *Salmonella typhi*, in Hajj pilgrims. Therefore, apart from just preventing Meningitis, it is also essential to prevent the Hajj pilgrims from potential typhoid fever caused due to *Salmonella typhi*. The Centre for Disease Control and Prevention, a federal agency under the Department of Health and Human Services in United States has recommended vaccination for both Typhoid as well as Meningitis before travelling to the African meningitis belt. Further, the pilgrims going to Hajj or Umrah are compulsorily required to receive meningococcal vaccine, without which the visa for Hajj is not issued. Moreover, typhoid vaccines are recommended before making the journey. Therefore a combination vaccine that simultaneously satisfy this kind of a requirement, wherein travelers are immunized at the same time against meningitis and typhoid would reduce the necessity of taking two separate vaccines. Rather, the traveler or the pilgrim needs to get vaccinated by the combination vaccine so as to satisfy the requirements and increase vaccine compliance.

Meningococcal vaccines require bacterial fermentation of the polysaccharides using animal media and alcohol for downstream processing. Usage of animal sources of porcine origin and alcohol limits the applicability of Meningitis vaccine by several Hajj pilgrims, because there exists a possibility of retention of the animal components and alcohol in the final finished vaccine product. Intake of any product of porcine origin and using alcohol is forbidden under Islamic Shariat laws, considered as 'HARAM' in colloquial language. Hence, as a matter of personal choice, a majority of the Muslim population opts not to get vaccinated with the existing meningitis vaccines because of using porcine material in the fermentation media and further downstreaming through alcohol derived substances. Moreover, the product development of vaccine formulations against individual Meningococcal infections are expensive due to use of alcohols and animal resources used as raw materials in the bacterial fermentation and downstream processes. To overcome this situation, synthetic and semi synthetic medium free from animal source has been utilized for cultivation of *Neisseria meningitidis* in general.

Along with usage of such synthetic and semi-synthetic media, it has also been aimed to increase yield of the bacterial fermentation using various media sources in the prior state of the art. Different media compositions has been described in non-patent literature as mentioned in Frantz, *J. Bact.,* 43:757-761.1942; and Catlin, *J. Inf. Dis.,* 128(2):178-194, 1973: *Watson Scherp Medium: J. Immunol* 1958; 81:337-44. A modified media was used in Frantz and Catlin 6 *Braz. J. Microbiol.* 34: 2003. New Chemically Defined Medium (NCDM) is described by David bundal et al. *JBC* 1974 which resulted in Men X polysaccharide yield of 20 mg/L. There were several other prior arts available describing the media composition and cultivation strategies for increasing the capsule polysaccharide yield. The fermentation is carried out in batch and fed batch modes with different feeding strategy(ies) based on pH stat, spiking and constant rate as per the requirements of the cultivation of Meningitidis A, C, Y, W135, and X strains (henceforth represented as Men A, Men C, Men Y, Men W135, and Men X respectively). Some of these relevant prior arts are being discussed herein. Prior art U.S. Pat. No. 7,399,615 discloses omitting $NH_4Cl$ from fermentation media and replacing it with soy peptone (HSP-A; Nutricepts, inc; Minneapolis, Minn.). The fed batch 2 L fermentation batch with feed solution containing Heat shock protein HSP-A resulted in Men A polysaccharide yield of 1300-1400 mg/L at a maximum Optical Density (OD) between 14-20. Prior art U.S. Pat. No. 7,491,517 disclosed *Neisseria meningitidis* fastidious culture medium (NMFM) with $CaCo_3$ to maintain pH 6.5 to 7.0 resulting in average yield of 30-40 mg/L with average OD of 10. Prior art WO2014/080423A2 disclosed the use of Casamino Acid instead of soy peptone or Yeast extract with novel feeding strategy using Feed Solution 1, (FS-1); and Feed Solution 2, (FS-2). To get Men X polysaccharides yield of 650 mg/L at 100 kDa stage when culture was harvested at a stage when culture OD is less than 60% of highest culture OD. The highest culture OD obtained was 16 at 580 nm.

The available fermentation medium and feed solutions described in prior arts utilized for cultivation and improving the yield of polysaccharide from serogroup A, C, Y, W135 and X had contributed only to some extent to increase the polysaccharide yield. But still there exists further requirement(s) of increasing the yield and decreasing the manufacturing cost of *Neisseria meningitidis* bacterial polysaccharides of all the strains viz. Men A, Men C, Men Y, Men W135, and Men X, for the purpose of making meningococcal vaccines further affordable and cost effective as well. The present invention is oriented to develop novel method(s) of increasing the bacterial polysaccharide of yield(s) of Men A, Men C, Men Y, Men W135, and Men X by using improved fermentation medium compositions containing peptones of non animal origin and utilizing novel feed components, and new methods of downstream processing and industrial purification of bacterial polysaccharides of *Neisseria meningitidis.*

The vaccine formulations developed in this patent application specifically finds its application to the HAJJ pilgrims, who bear very high amount of risk of contracting infections from Meningitidis bacteria and typhoid fever, both of which are preventable through appropriate effective vaccination strategy comprising respective bacterial capsular polysaccharides as the vaccine antigens in a single combination vaccine including typhoid conjugate vaccine antigen. As already seen earlier, that none of the available meningitis vaccines cover all the existing serotypes of the disease. So, protection remains incomplete in almost every individual including even those who underwent vaccination against meningitis. Furthermore, a complete combination of all major existing serotypes of meningitis will comply with complete protection against meningitis for any individual hailing from any region of the World. Additionally, as there are no possibility(ies) of including any media components derived from animal origin, and alcohol, therefore, it is advantageous to term such a novel combination vaccine for Haj pilgrims, as a 'HALAL' vaccine preferably branded as HAJVAC™ by the patent applicant. Conjugate polysaccharide vaccines has been already developed specific to particular serotypes of Meningitidis infections, for long term immunity against the given serotypes. But, as said earlier conjugate vaccines does not ensure complete protection against all serotypes of the vaccine. Therefore, it is suggested that a polysaccharide based vaccine is adequately immunogenic to confer protection against any possible infection by any one or more of meningitidis or *Salmonella typhi* infections. The immunity conferred by polysaccharide vaccines last for a period of 2 years, and hence it is sufficient to justify the applicability of combined polysaccharide based vaccines as enumerated in this invention along with Vi polysaccharide conjugate typhoid vaccine antigen which are sufficient to ensure complete protection to the subjects in areas of high conglomeration of travelers in a specific geographic location.

BRIEF DESCRIPTION OF THE DRAWINGS

FIG. 1: Growth Kinetics of *N. meningitidis* serotype A 200 L fermentation batch taken with two Shot feeding strategy.

FIG. 2: Growth Kinetics of *N. meningitidis* serotype C 200 L fermentation batch taken with two Shot feeding strategy.

FIG. 3: Growth Kinetics of *N. meningitidis* serotype Y 200 L fermentation batch taken with two Shot feeding strategy.

FIG. 4: Growth Kinetics of *N. meningitidis* serotype W135 200 L fermentation batch taken with two Shot feeding strategy.

FIG. 5: Growth Kinetics of *N. meningitidis* serotype X 200 L fermentation batch taken with two Shot feeding strategy.

FIG. 6: Growth Kinetics of *N. meningitidis* serotype A 200 L fermentation batch taken with continuous feeding mode.

FIG. 7: Growth Kinetics of *N. meningitidis* serotype C 200 L fermentation batch taken with continuous feeding mode.

FIG. 8: Growth Kinetics of *N. meningitidis* serotype Y 200 L fermentation batch taken with continuous feeding mode.

FIG. 9: Growth Kinetics of *N. meningitidis* serotype W135 200 L fermentation batch taken with continuous feeding Mode.

FIG. 10: Growth Kinetics of *N. meningitidis* serotype X 200 L fermentation batch taken with continuous feeding Mode.

FIG. 11: Total CPS concentration of *N. meningitidis* Serogroup A at 100 kd stage using a range of concentration of sucrose between 0-25% with 0.06 mM LL37 in the feed composition.

FIG. 12: Total CPS concentration of *N. meningitidis* Serogroup C at 100 kd stage using a range of concentration of sucrose between 0-25% with 0.06 mM LL37 in the feed composition.

FIG. 13: Total CPS concentration of *N. meningitidis* Serogroup Y at 100 kd stage using a range of concentration of sucrose between 0-25% with 0.06 mM LL37 in the feed composition.

FIG. 14: Total CPS concentration of *N. meningitidis* Serogroup W135 at 100 kd stage using a range of concentration of sucrose between 0-25% with 0.06 mM LL37 in the feed composition.

FIG. 15: Total CPS concentration of *N. meningitidis* Serogroup X at 100 kd stage using a range of concentration of sucrose between 0-25% with 0.06 mM LL37 in the feed composition.

OBJECTIVES OF THE INVENTION

The primary objective of the invention is to provide an immunological composition for complete prophylaxis against meningococcal diseases caused by pathogenic *Neisseria meningitidis.*

Another objective of the invention is to provide an immunological composition for prophylaxis against typhoid fever caused by pathogenic *Salmonella typhi.*

Yet another objective of the present invention is to provide a combination vaccine comprising multiple polysaccharide vaccine antigens for protecting a subject against meningococcal diseases caused by all pathogenic serotypic forms of *Neisseria meningitidis* and typhoid fever caused by pathogenic *Salmonella typhi.*

Another objective of the present invention is to provide an immunological composition for prophylaxis against meningococcal diseases caused by all five types of distinct antigenic capsular groups of *Neisseria meningitidis* which are responsible for invasive meningitis and septicaemia.

A further objective of the present invention is to provide for a method of getting an increased capsular polysaccharide yield by using an improved fermentation medium of non-animal origin, an improved method of downstream processing and industrial purification of bacterial polysaccharide, hence constituting a technical advance over the prior art.

Another objective of the present invention is to provide a highly effective, yet cost-effective vaccine against all serotypes of meningococcal diseases as well as typhoid fever, which is affordable for especially lower-middle income and low-income economy countries.

A specific objective of the present invention is to provide a vaccine for international travelers, for prevention against all forms of non-endemic meningococcal diseases as well as typhoid fever.

Another specific objective of the present invention is to provide for a vaccine which can be used by Hajj pilgrims for prophylaxis against all forms of meningococcal diseases along with typhoid fever, which might be transmitted due to the diverse conglomeration during the pilgrimage.

SUMMARY OF THE INVENTION

The present invention provides for a composition and method of manufacture of combined vaccine formulations wherein the said combination vaccine is effective against different serotypes of *Neisseria meningitidis* and *Salmonella typhi* Vi polysaccharide conjugate antigens.

In one aspect, the invention provides a stable and effective vaccine formulation comprising bacterial capsular polysaccharides of *Neisseria meningitidis* stereotype A, Y, C, W-135 and X which may comprise an additional *Salmonella typhi* Vi polysaccharide (either plain polysaccharide or Vi polysaccharide conjugated to tetanus toxoid vaccine antigen).

In a further aspect, the invention provides a method of obtaining the bacterial capsular polysaccharides by a fed-batch process which comprises:

using improved compositions for Yeast Extract based media composition (BBIL-YE), Soy peptone based media composition (BBIL-SP) and Vegetable infusion peptone based media composition (BBIL-VI);

using a novel feed composition which comprises of sucrose, cationic peptide LL37, Sodium glutamate, Arginine, Serine, L-Cysteine, Magnesium chloride and Ferrous citrate, in a novel two shot feeding strategy or by continuous feed;

downstream processing for capsular polysaccharide through protein precipitation techniques by the use of either singly or in combination of Zinc acetate, Disodium Hydrogen Phosphate, Sodium Dihydrogen Phosphate and/or Sodium citrate.

According to the embodiments provided in this invention, the advantages of the improved media and the fed-batch mode either through continuous mode, or 2-shot feeding strategy which are clearly illustrated herein, shows up to 14-fold increase in the crude polysaccharide concentration as compared to other conventionally used media for industrial production of bacterial polysaccharides. Further, while scaling-up the process at 200 L, the yield loss of bacterial polysaccharide is found to be negligible, that also highlights particular advantages of the present invention.

In another embodiment of the embodiment of the invention, the process of downstream processing and purification of capsular polysaccharides through protein precipitation techniques by any one of Zinc acetate, or in combination of Zinc acetate with Disodium Hydrogen Phosphate and Sodium Dihydrogen Phosphate, or Sodium citrate alone.

In an embodiment of the invention, immunogenecity of the vaccine formulations are provided. It is established that the immunogenicity of all the individual vaccine antigens *Neisseria meningitidis* stereotype A, Y, C, W135 and X and Vi-polysaccharide conjugate are not interfered by the presence of other antigens.

Further an embodiment of the invention, the stability of meningococcal polysaccharides and polysaccharide conjugate vaccine compositions are provided.

DETAILED DESCRIPTION OF THE INVENTION

As discussed above, the present invention describes novel media compositions for industrial fermentation of bacterial polysaccharides of *Neisseria meningitidis*, which are of non-animal origin. The media compositions of the present invention are developed comprising either of yeast-extract based media composition (named hereinafter as BBIL-YE), or soy-peptone based media composition (named hereinafter as BBIL-SP), or vegetable infusion protein based media composition (named hereinafter as BBIL-VI) for production of industrial polysaccharides. Further, this present invention describes novel feed compositions in a fed-batch mode of bacterial fermentation of industrial polysaccharides of *Neisseria meningitidis*. The feed in the present invention is provided either following a two shot strategy by incorporating the feed contents at a fixed proportion at particular fixed time intervals during when the fermentation is already undergoing and/or allowing continuous feed through out the fed-batch mode of fermentation. The present invention is based on the fact that inclusion of sucrose in media helps in formation of biofilms by gram positive and gram negative pathogenic bacteria. The major biofilm components are the extracellular matrix composed of polysaccharides. Another component that includes in the media during bacterial cultivation is cationic peptide LL37 which is reported to upregulate genes siaC and siaD responsible for capsule production in *Neisseria meningitidis* (Jones, A. et al. 2009. JBC. 191: 3861-3868). Thus looking into the prospects of utilizing sucrose as a carbon source to support the formation of capsular polysaccharide along with antibiotics such as selected from polymexine-B, or LL37 which specifically upregulates the expression of capsular polysaccharide producing genes to increase the formation of yield of polysaccharide which has been confirmed through appropriate experimentations in Shake flasks and at industrial scales to evaluate the use of Sucrose along with LL37 as a feed. The bacterial fermentation of the meningococcal strains has been done wherein the strains are obtained from the depository of Culture Collection, Department of Clinical bacteriology, University of Goteborg, Sweden, and named as CCUG-55614 for *Neisseria meningitidis* X, CCUG-42379 for *Neisseria meningitidis* A, CCUG32912 for *Neisseria meningitidis* C, CCUG-38303 for *Neisseria meningitidis* Y and CCUG-41485 for *Neisseria meningitidis* W135.

Subsequently, the present invention also discloses further improved methods of downstream processing to obtain safe bacterial capsular polysaccharides for vaccine productions mainly *Neisseria meningitidis* A, *Neisseria meningitidis* Y, *Neisseria meningitidis* C, *Neisseria meningitidis* W135 and *Neisseria meningitidis* X capsular polysaccharide(s) for vaccine formulation, the said bacterial fermentation, cultivation and downstream purification techniques completely eliminates the use of any components of animal origin and alcohol, thereby ensuring absolute compliance respect to the religious sentiments of various ethnic groups particularly Islamic nations, where such bacterial infections are highly endemic in nature.

Example 1: Fermentation Process

The media optimized in shake flask experiments for specific *Neisseria meningitidis* serotypes was used for fermentation in 200 L medium in a 300 L bioengineering fermenter. Primary seed was prepared by re suspending the culture grown on chocolate agar plate or Muller Hinton agar plate incubated at 36.0±1° C. with ~5% $CO_2$ in candle jar for 18-24 hrs in 100 ml fermentation medium and incubating at 36.0±1° C. on 150 rpm. Primary seed of 8-10 hr stage was transferred to 900 ml fermentation media and further incubated at 36.0±1° C. on 150 rpm for 12-18 hrs or till optical density (OD) reaches 5 at 600 nm. One liter secondary seed was inoculated to 9 L of fermentation media in 18 L bioengineering fermenter. The final 10 liter seed of Optical Density of 10 at 600 nm was used to inoculate 200 L of final fermentation medium in 300 L bioengineering fermenter.

Fermentation parameters are explained in Table 2.

TABLE 2

Fermentation Parameters

| Parameter | Unit |
|---|---|
| Temperature | 36.0 ± 1° C. |
| Agitation | 150-600 rpm |
| pH | 7.0 ± 0.5 |
| Dissolved Oxygen | 25% to 90% |
| Aeration | 0.5-2 VVM |
| Pressure | ~0.2 bar |

Example 2: Media Composition and Preparation

The cultivation of *Neisseria meningitidis* stereotype A, Y, C, W135 and X is based on seed lot system and grown in an improved media compositions disclosed in the Table 3, 4 and Table 5 below.

TABLE 3

Yeast Extract based media composition (BBIL-YE)

| Composition | Concentration (gm/L) |
|---|---|
| Ammonium chloride | 0.1-2.0 |
| Glutamic Acid | 5-20 |
| Serine | 0.25 to 0.4 |
| Arginine | 0.25 to 0.4 |
| L-Cysteine | 0.2 to 0.3 |
| Dipotasium Hydrogen Phosphate | 4 |
| Sodium Chloride | 5 |

TABLE 3-continued

| Yeast Extract based media composition (BBIL-YE) | |
|---|---|
| Composition | Concentration (gm/L) |
| Magnesium sulphate | 0.73 |
| Calcium chloride | 0.03 |
| Ferrous citrate | 0.04 |
| Yeast Extract | 5-20 |
| Glucose | 10-20 |

TABLE 4

| Soy peptone based media composition (BBIL-SP) | |
|---|---|
| Composition | Concentration (gm/L) |
| Ammonium chloride | 0.1-2.0 |
| Glutamic Acid | 5-20 |
| Serine | 0.25 to 0.4 |
| Arginine | 0.25 to 0.4 |
| L-Cysteine | 0.2 to 0.3 |
| Dipotasium Hydrogen Phosphate | 4 |
| Sodium Chloride | 5 |
| Magnesium sulphate | 0.73 |
| Calcium chloride | 0.03 |
| Ferrous citrate | 0.04 |
| Soy peptone | 5-20 |
| Glucose | 10 |

TABLE 5

| Vegetable infusion peptone based media composition (BBIL-VI) | |
|---|---|
| Composition | Concentration (gm/L) |
| Ammonium chloride | 0.1-2.0 |
| Glutamic Acid | 5-20 |
| Serine | 0.25 to 0.4 |
| Arginine | 0.25 to 0.4 |
| L-Cysteine | 0.2 to 0.3 |
| Dipotassium Hydrogen Phosphate | 4 |
| Sodium Chloride | 5 |
| Magnesium sulphate | 0.73 |
| Calcium chloride | 0.03 |
| Ferrous citrate | 0.04 |
| Vegitable Infusion peptone (30 k diafiltered) | 5-20 |
| Glucose | 10 |

These particular media compositions as disclosed in this invention are applicable for commercial cultivation and fermentation for all types of bacterial capsular polysaccharides. As examples, the inventors have shown that these media composition are responsible for higher yields for particular serotypes of bacterial capsular polysaccharides of *Neisseria meningitidis*. Yet, it should not be understood that this media compositions is limiting to only those given polysaccharides. Persons skilled in the art will acknowledge that examples provided in this application are only for support of the invention and not to limit the scope of the invention at all. The media compositions and the downstream processing methodologies will also be effective for providing higher yields of other serotypes of the same microorganisms presented herein, and also for fermentation and cultivation of any capsular polysaccharides from any bacteria particularly *H. influenzae* type b CS 68 strain, *Neisseria meningitidis* serotypes A, C, Y, W135 and X, *Streptococcus pneumoniae* serotype 9V, *Salmonella typhi* and *Salmonella paratyphi.*

Media Preparation:

(a) Any of the three media composition(s) of the present invention of non animal origin (BBIL-YE, BBIL-SP and BBIL-VI) was thoroughly dissolved in 1 in $10^{th}$ volume of water for injection (total batch quantity of 10 liters) and diafiltered using 30 KDa cassette to remove unwanted high molecular weight impurities. This eliminates high molecular weight unwanted impurities, thereby enhancing the growth and decreases the possibilities of interference of impurities during the subsequent purification steps.

(b) Media was prepared by dissolving following components in same order Ammonium chloride, Sodium Chloride, Dipotassium Hydrogen Phosphate, Magnesium sulphate, Calcium chloride, Ferrous citrate, Serine, Arginine, L-Cysteine, Glutamic acid and finally adding filtered peptone of non animal origin.

(c) Media was sterilized by autoclaving at 121° C. for 15 min in fermenter.

(d) Glucose and Magnesium sulphate is dissolved and sterilized separately by autoclaving at 121° C. for 15 min and added to the base media composition asceptically in fermenter and pH was adjusted to 7.0.+−0.0.2 using 1M Sodium hydroxide (NaOH) solution.

Example 3: Novel Feed Composition, Preparation and Feeding Strategy and Growth Kinetics Novel Feed Composition The novel feed composition is comprised of sucrose 0.5 to 50%, Sodium glutamate (up to 10 gm/l) and cationic peptide LL37 from 0.5 to 20 μg/ml of total fermentation media depending on the cultivation of the *N. meningitidis* strain. Other components of feed composition are constant and presented in Tables 6 and 7.

TABLE 6

| Feed composition-1 | |
|---|---|
| Component | Concentration (gm/l) |
| Sucrose | 0.5-50% |
| Sodium glutamate | 10-50 |
| LL37 | 0.0005-0.02 |
| Arginine | 0-10 |
| Serine | 0-10 |
| L-cysteine | 0-5 |
| Magnesium chloride | 2 |
| Ferrous citrate | 0.04 |

TABLE 7

| Feed composition-2 | |
|---|---|
| Component | Concentration (gm/l) |
| Sucrose | 0.5-50% |
| Sodium glutamate | 0-60 |
| LL37 | 0.0005-0.02 |
| Magnesium chloride | 2-4 |

Feed Preparation (a) Sucrose, Sodium glutamate and other feed components except cationic peptide LL37 were dissolved in 10 liters of WFI and autoclaved at 121° C. for 15 min in a 10 L (b) bottle with siphon attachment.

(c) Cationic peptide was filtered through 0.22μ filter and added aseptically to above mentioned composition.

Feeding Strategy

Novel two shot feeding strategy and Continuous feeding mode was evaluated for achieving higher polysaccharide yield. The 50% of feed solution was fed to the batch at $4^{th}$ hr and another 50% feed was added at $6^{th}$ hr of the fermentation process while maintaining the pH at 7.1±0.2 and Dissolved oxygen (DO) above 30%. The fermentation was carried out for more 4 hrs and finally harvested at $10^{th}$ hr by adding 0.6% formalin and continuing further 3 hrs followed by rapid chilling at 15° C. and harvesting of inactivated culture broth. The FIGS. 1 to 5 represent the results of *N. meningitidis* fermentation carried out at 200 L fermentor using optimized two shot strategy. The FIG. 6 to 10 are representing results of continuous feeding.

In FIGS. 1 to 5, the sugar concentration during bacterial fermentation is represented as bar graphs at a unit of gm/l. There is a slow decrease in the sugar concentration from $1^{st}$ hour to $4^{th}$ hour. At $4^{th}$ hour, first feed shot is given to the fermentation media. This increases the sugar concentration at $5^{th}$ hour, and then again there is a decrease in the sugar concentration of the fermentation media at $6^{th}$ hour. At $6^{th}$, hour the second feed shot is provided. As mentioned above since the feed comprises of Sucrose, Sodium glutamate and LL37, the sugar concentration immediately increases immediately after the feed shot. Then, the sugar concentration again increases and is followed by slow decrease in the sugar concentration from $6^{th}$ hour till harvest. The optical density is plotted at every hour during the bacterial fermentation represented in the FIGS. 1 to 5 as a continuous line, till harvest. The optical density measured at 600 nm is a measure of the growth kinetics of the bacterial fermentation in the figures.

In FIGS. 6 to 10, the sugar concentration during bacterial fermentation is represented as bar graphs at a unit of gm/l. There is a slow decrease in the sugar concentration from $1^{st}$ hour to $4^{th}$ hour. Feed is provided between $4^{th}$ to $7^{th}$ hour through gradual increase in sugar concentration in the fermentation media depending upon the optical density and flow rate of the fermentation process. As mentioned above since the feed comprises of Sucrose, Sodium glutamate and LL37, the sugar concentration shows a gradual increase during feed injection from $4^{th}$ to $7^{th}$ hour. This is followed by slow decrease in the sugar concentration from $8^{th}$ hour till harvest. The optical density is plotted at every hour during the bacterial fermentation represented in the FIGS. 6 to 10 as a continuous line, till harvest. The optical density measured at 600 nm is a measure of the growth kinetics of the bacterial fermentation in the FIGS. 6-10. For continuous feed, the feed composition as detailed in Table 6 has been given during bacterial fermentation.

Example 4: Results and Scale-Up from Shake Flask to 200 Liter Batch

First of all the optimized concentration of sucrose over the range of 0.5-50% and LL37 0.5-20 µg/ml was determined in shake flask experiments for *N. meningitidis* serotype A, Y, C, W135 and X. Shake flask experiments were carried out in total volume of 200 ml media contained in 1 L flask with constant rpm of 150 at 37° C. Based on the results of shake flask experiments, optimized concentrations of Sucrose and LL37 was utilized in 10 L fermentation carried out in 18 L bioengineering fermenter and further scaled up to 200 liters in 300 liter bioengineering fermenter. The results presented in Table 9 is represented for 10 L and 200 L fermentation batch taken for *N. meningitidis* strain A, C, Y, W135 and X. Table 8 is represents the cell growth and polysaccharide yield obtained in shake flask experiments of modified Sucrose feed media in comparison with reference media of Frantz (Ref) and Catlin 6 (Ref) media separately. Additionally, the effect of various concentrations of the feed composition including Sucrose with standardized LL37 concentration has been explained in FIGS. 11 to 15. The maximum harvest obtained with the most optimum Sucrose concentrations in the feed media that produces the maximum harvest of crude polysaccharide (represented as black bars) are shown in FIGS. 11-15. The corresponding results for crude bacterial polysaccharide harvest after initial removing of unwanted media components, salts, and other residual matters through a 100 kDa Tengential Flow Filtration Stage are tabulated in Table 9.

TABLE 8

Total capsular polysaccharide production by *N. meningitidis* serotypes harvested from 200 ml shake flask experiments utilizing 30 KD filtered yeast extract (BBIL-YE) as peptone source.

| | | Frantz | | Catlin 6 | | Feed Media of the present invention | |
|---|---|---|---|---|---|---|---|
| S. No. | Serotype Name | OD at 600 nm | PS µg/ml | OD 600 nm | PS µg/ml | OD 600 nm | PS µg/ml |
| 1 | *N. meningitidis* A | 4.0 ± 1 | 21 ± 1 | 4.2 ± 1 | 45 ± 1 | 11.8 ± 2 | 136 ± 1 |
| 2 | *N. meningitidis* C | 4.1 ± 2 | 21 ± 1 | 4.8 ± 2 | 42 ± 1 | 12.8 ± 1 | 180 ± 1 |
| 3 | *N. meningitidis* Y | 4.2 ± 1 | 23 ± 2 | 5.2 ± 1 | 34 ± 2 | 14.2 ± 1 | 290 ± 1 |
| 4 | *N. meningitidis* W135 | 5.8 ± 1 | 33 ± 2 | 6.5 ± 1 | 51 ± 2 | 15.8 ± 1 | 489 ± 1 |
| 5 | *N. meningitidis* X | 4.2 ± 1 | 23 ± 1 | 4.3 ± 1 | 47 ± 1 | 12.7 ± 2 | 340 ± 2 |

Therefore, from above Table 8, we can compare the amount of polysaccharide obtained using BBIL novel media compositions and novel feed as against conventionally used media compositions ‘Frantz’ and ‘Catlin 6’.

In 200 ml shake flask experiments, *N. meningitidis* A showed polysaccharide content of 136±1 µg/ml at an $OD_{600}$ of 11.8±2 for the novel media and feed according to the methods disclosed under this invention as compared to 45±1 µg/ml at an $OD_{600}$ of 4.2±1 for Catlin 6 media, and merely 21±1 µg/ml at an $OD_{600}$ of 4.0±1 for Frantz media. Therefore, we see that the fold increase in at least 6 folds increase or at least 3 folds increase in crude polysaccharide yield for the methods disclosed under this present invention undergoing the novel feed media of this present invention as compared to conventional Frantz media, and Catlin 6 media respectively.

In 200 ml shake flask experiments, *N. meningitidis* C showed polysaccharide content of 180±1 µg/ml at an $OD_{600}$ of 12.8±1 for the novel media and feed according to the methods disclosed under this invention as compared to 42±1 μg/ml at an $OD_{600}$ of 4.8±2 for Catlin 6 media, and merely 21±1 μg/ml at an $OD_{600}$ of 4.1±2 for Frantz media. Therefore, we see that the fold increase in at least 8 folds increase or at least 5 folds increase in crude polysaccharide yield for the methods disclosed under this present invention undergoing the novel feed media of this present invention as compared to conventional Frantz media, and Catlin 6 media respectively.

In 200 ml shake flask experiments, *N. meningitidis* Y showed polysaccharide content of 290±1 μg/ml at an $OD_{600}$ of 14.2±1 for the novel media and feed according to the methods disclosed under this invention as compared to 34±2 μg/ml at an $OD_{600}$ of 5.2±1 for Catlin 6 media, and merely 23±2 μg/ml at an $OD_{600}$ of 4.2±1 for Frantz media. Therefore, we see that the fold increase in at least 12 folds increase or at least 8 folds increase in crude polysaccharide yield for the methods disclosed under this present invention undergoing the novel feed media of this present invention as compared to conventional Frantz media, and Catlin 6 media respectively.

In 200 ml shake flask experiments, *N. meningitidis* W135 showed polysaccharide content of 489±1 μg/ml at an $OD_{600}$ of 15.8±1 for the novel media and feed according to the methods disclosed under this invention as compared to 51±2 μg/ml at an $OD_{600}$ of 6.5±1 for Catlin 6 media, and merely 33±2 μg/ml at an $OD_{600}$ of 5.8±1 for Frantz media. Therefore, we see that the fold increase in at least 14 folds increase or at least 9.folds increase in crude polysaccharide yield for the methods disclosed under this present invention undergoing the novel feed media of this present invention as compared to conventional Frantz media, and Catlin 6 media respectively.

In 200 ml shake flask experiments, *N. meningitidis* X showed polysaccharide content of 340±2 μg/ml at an $OD_{600}$ of 12.7±2 for the novel media and feed according to the methods disclosed under this invention as compared to 47±1 μg/ml at an $OD_{600}$ of 4.3±1 for Catlin 6 media, and merely 23±1 μg/ml at an $OD_{600}$ of 4.2±1 for Frantz media. Therefore, we see that the fold increase in at least 14 folds increase or at least 7 folds increase in crude polysaccharide yield for the methods disclosed under this present invention undergoing the novel feed media of this present invention as compared to conventional Frantz media, and Catlin 6 media respectively.

TABLE 9

Total capsule polysaccharide production by *N. meningitidis* serotypes harvested from 10 L and 200 L fermenter utilizing 30 kd filtered yeast extract (BBIL-YE) as peptone source.

| S. No. | Serotype Name | Sucrose | LL37 Conc. | Harvesting Time | Yield of 10 Ltr at 100 KDa TFF stage in mg/L | Yield of 200 Ltr at 100 KDa TFF stage in mg/L |
|---|---|---|---|---|---|---|
| 1 | *N. meningitidis* A | 7.50% | 0.06 mM | 10 hrs | 2227 | 1960 |
| 2 | *N. meningitidis* C | 7.50% | 0.12 mM | 10 hrs | 1820 | 1680 |
| 3 | *N. meningitidis* Y | 7.50% | 0.12 mM | 10 hrs | 1670 | 1520 |
| 4 | *N. meningitidis* W135 | 7.50% | 0.12 mM | 10 hrs | 1650 | 1510 |
| 5 | *N. meningitidis* X | 7.50% | 0.06 mM | 10 hrs | 1510 | 1430 |

Comparative Polysaccharide Harvest with Three Different Media Compositions (BBIL-YE, BBIL-SP and BBIL-VI) Concentration of 100 kDa Stage Polysaccharides content of *N. meningitidis* strain W135 cultivated in three different peptone source of non animal origin are provided in Table 10 below.

TABLE 10

Polysaccharide concentrations of Men W135 of 10 liter batch

| Nitrogen source utilized | Sucrose % | LL37 μg/ml | Polysaccharide concentration mg/ml |
|---|---|---|---|
| Soy peptone (BBIL-SP) | 0.5-50% | 0.5-20 | 1420 |
| Yeast extract (BBIL-YE) | 0.5-50% | 0.5-20 | 1650 |
| Vegetable infusion peptone (BBIL-VI) | 0.5-50% | 0.5-20 | 1570 |

Example 5: Inactivation and Harvesting

Fermentation batch was harvested when three consecutive reading taken at the interval of 30 minutes are same over the period of $7^{th}$ to $12^{th}$ hr. For inactivating the culture 0.5 to 0.8% formalin was used depending on the *N. meningitidis* strain. Culture was incubated 36.0±1° C. for 3 hours after addition of formalin. The culture broth was cooled down to 10-15° C. in fermenter. Chilled culture broth was collected in sterile bottles and the broth was harvested by centrifugation followed by 0.22μ filtration.

Example 6: Downstream Processing and Purification of Bacterial Polysaccharides

Inactivated and harvested broth is centrifuged at 4000 RPM for 30 minutes. Cell pellet was discarded. The cell free supernatant was subjected to 100 kDa Tangential Flow Filtration (TFF) for removal of unwanted media components and residual matters.

Then, the retentate was subjected to protein precipitation for removal of proteins using Zinc acetate (at a range of 0.5% to 5% w/v), preferably the Zinc acetate precipitation was done at the range of 1% to 3% w/v. More preferably Zinc acetate precipitation was performed at 1.8% to 2.5% w/v. The results of protein precipitation with 2% w/v Zinc Acetate are provided in the Table 11 below.

Alternatively, the retentate was subjected to protein precipitation for removal of proteins using a combination of Zinc acetate (0.5% to 5% w/v) and mixture of 25 mM Disodium Hydrogen Phosphate & 25 mM Sodium Dihydrogen Phosphate, preferably the Zinc acetate used was at the range of 1% to 3% w/v. More preferably Zinc acetate was used at 2% to 2.5% w/v. The results of protein precipitation using combination of Zinc acetate at 2% w/v, 25 mM Disodium Hydrogen Phosphate & 25 mM Sodium Dihydrogen Phosphate are provided in the Table 12 below.

Alternatively, the retentate was subjected to protein precipitation for removal of proteins using Sodium citrate (0.5M to 1.0M) alone. The results of protein precipitation are provided in the Table 13 below.

Alternatively, the retentate was subjected to protein precipitation for removal of proteins using a combination of Zinc acetate (0.5% to 5% w/v) and Sodium citrate (0.5M to 1.0M), preferably the Zinc acetate precipitation was done at the range of 1% to 3% w/v. More preferably Zinc acetate precipitation was performed at 1.8% to 2.5% w/v.

Alternatively the protein was precipitated using by Ammonium sulphate or Sodium citrate with final concentration of 30-70% v/v with or without Zinc acetate. Any salt combination mentioned in Hofmeister series or lyotropic series can also be alternatively used.

This was followed by centrifugation and the palate was discarded. Supernatant was passed through 100 kDa TFF to remove residual salts. The retentate was then subjected to enzyme treatment for further degradation of residual proteins and/or nucleic acid materials. Suitable enzymes used for enzyme treatment includes but not limited to benzonase, protease, RNAase, DNAase etc. Enzyme treatment would degrade such proteins or other nucleic acid materials which are above 100 kDa size. Other enzyme like DNAs, RNAs Proteinase K or Nargase can alternatively be used instead of Benzonase. Benzonase treatment was given at 37° C. for 8-12 hrs. Benzonase treated supernatant was further subjected to diafiltration and concentrated using 50 mM Tris HCl buffer at pH 7.0 through 100 KDa TFF cassette for removal of the components below 100 KDa size as the size of the polysaccharide of interest is above 100 KDa. Entire concentrated solution was diafiltered for 24 hrs in 10 KDa TFF against WFI. The final solution was lyophilized. The whole process was performed without using ethanol completely. The retentate was then lyophilized and reconstituted to undergo further stages of chromatographic purification. Further purification of lyophilized polysaccharide was achieved by CHT Ceramic Hydroxy Apatite Raisin (simultaneous anion and cation exchange chromatography). The bacterial polysaccharides may be purified by at least one of the following methods i.e. to say ion exchange chromatography, gel filtration, affinity chromatography, hydrophobic column chromatography, fractionation with salt, organic solvent(s); centrifugation etc can also be implemented for purification and downstream processing without use of any alcohol at all.

TABLE 11

Removal of protein impurities by Zinc acetate (0.5-5%) precipitation in 10 liter batch.

| | 100 KDa TFF stage before Zinc acetate treatment | | 100 KDa TFF stage after Zinc acetate (0.5-5%) treatment (2%) | | Final bulk | |
|---|---|---|---|---|---|---|
| Meningococcal Serotype | Total Capsular Polysaccharide (mg/ml) | Total Protein % | Total Capsular Polysaccharide (mg/ml) | Total Protein % | Total Capsular Polysaccharide (mg/ml) | Total Protein % |
| *N. meningitidis* A | 2227 | 40-65 | 2117 | <5 | 1932 | 0.15 |
| *N. meningitidis* C | 1850 | 35-58 | 1810 | <5 | 1520 | 0.12 |
| *N. meningitidis* Y | 1640 | 50-62 | 1620 | <5 | 1360 | 0.09 |
| *N. meningitidis* W135 | 1630 | 40-58 | 1590 | <10 | 1342 | 0.13 |
| *N. meningitidis* X | 1580 | 38-65 | 1510 | <5 | 1210 | 0.14 |

TABLE 12

Removal of protein impurities by Zinc acetate (0.5-5%) along with 25 mM each of Disodium Hydrogen Phosphate and Sodium Dihydrogen Phosphate precipitation in 10 liter batch.

| | 100 KDa TFF stage before Zinc acetate treatment | | 100 KDa TFF stage after Zinc acetate (0.5-5%) with 25 mM each $Na_2HPO_4$ and $NaH_2PO_4$ treatment. | | Final bulk | |
|---|---|---|---|---|---|---|
| Meningococcal Serotype | Total Capsular Polysaccharide (mg/ml) | Total Protein % | Total Capsular Polysaccharide (mg/ml) | Total Protein % | Total Capsular Polysaccharide (mg/ml) | Total Protein mg/ml |
| *N. meningitidis* A | 2327 | 45-68 | 2127 | <5 | 1932 | 0.12 |
| *N. meningitidis* C | 1810 | 30-55 | 1800 | <5 | 1520 | 0.16 |
| *N. meningitidis* Y | 1680 | 55-70 | 1650 | <5 | 1360 | 0.17 |
| *N. meningitidis* W135 | 1660 | 45-58 | 1610 | <5 | 1342 | 0.14 |
| *N. meningitidis* X | 1540 | 30-65 | 1500 | <5 | 1210 | 0.06 |

TABLE 13

Removal of protein impurities by Sodium citrate 0.5-1M Concentration.

| | 100 KDa TFF stage before Zinc acetate treatment | | 100 KDa TFF stage after Sodium Citrate (0.5-1M) treatment | | Final bulk | |
|---|---|---|---|---|---|---|
| Meningococcal Serotype | Total Capsular Polysaccharide (mg/ml) | Total Protein % | Total Capsular Polysaccharide (mg/ml) | Total Protein % | Total Capsular Polysaccharide (mg/ml) | Total Protein mg/ml |
| *N. meningitidis* A | 2327 | 40-65 | 2137 | 15 | 1932 | 0.13 |
| *N. meningitidis* C | 1850 | 35-55 | 1830 | 20 | 1520 | 0.15 |
| *N. meningitidis* Y | 1610 | 50-70 | 1570 | 14 | 1360 | 0.14 |
| *N. meningitidis* W135 | 1670 | 40-58 | 1600 | 10 | 1342 | 0.15 |
| *N. meningitidis* X | 1540 | 35-60 | 1490 | 12 | 1210 | 0.08 |

Example 7: Vaccine Formulations

The bacterial polysaccharides manufactured through the processes developed in this invention described above are formulated along with a combination of bacterial polysaccharides of *Salmonella typhi* conjugated to a carrier protein and the bacterial polysaccharides of *Neisseria meningitidis* A, *Neisseria meningitidis* C, *Neisseria meningitidis* Y, *Neisseria meningitidis* W135 and *Neisseria meningitidis* X.

A stable vaccine composition for prophylaxis against infections caused by *Neisseria meningitidis* and *Salmonella typhi* comprising:

(a) vaccine antigens, the said vaccine antigens comprising capsular polysaccharides of *Neisseria meningitidis* A, *Neisseria meningitidis* C, *Neisseria meningitidis* Y, *Neisseria meningitidis* W135 *Neisseria meningitidis* X and *Salmonella typhi* Vi capsular polysaccharide conjugated to a carrier protein tetanus toxoid (ViPs-TT);

(b) a combination of sugars selected from sucrose, glucose, lactose, maltose and trehalose;

(c) a buffer selected from normal saline and phosphate buffer saline;

(d) a preservative; and (e) optionally an adjuvant;

wherein, the said formulations do not contain any animal component or alcohol.

Formulation-A1

The vaccine formulations as presented under this invention comprises of capsular polysaccharides of *N. meningitis* A, *N. meningitis* C, *N. meningitis* Y, *N. meningitis* W135 and *N. meningitis* X formulated and presented as lyophilized form with or without diluent buffers. The bacterial capsular polysaccharides of meningitidis A, C, Y, W135 and X are presented as lyophilized pellets. Diluent buffers of the vaccine formulations according to the present invention are selected from normal saline or phosphate buffered saline. The diluent buffer is formulated with NaCl or Sodium Phosphate buffer. Whereas lyophilized meningitidis A, C, Y, W135 and X formulation contains either combination of sugars selected from trehalose, sucrose and lactose as stabilizers.

Formulation-A2

The formulations as presented under this invention comprises of capsular polysaccharides of *N. meningitis* A, *N. meningitis* C, *N. meningitis* Y, *N. meningitis* W135 and *N. meningitis* X formulated and presented as lyophilized form with *Salmonella typhi* Vi polysaccharide conjugated to carrier protein tetanus toxoid (ViPs-TT). The bacterial capsular polysaccharides of meningitidis A, C, Y, W135 and X are presented as lyophilized pellets. The ViPs-TT vaccine antigen of the vaccine formulations according to the present invention are dissolved in normal saline or phosphate buffered saline. The diluent buffers are formulated with sodium chloride or sodium phosphate buffers. The lyophilized meningitidis A, C, Y, W135 and X formulation contains either combination of sugars selected from trehalose, sucrose and lactose as stabilizers. The vaccine formulations might further contain preservatives such as thiomersal.

Formulation-A3

The formulations as presented under this invention comprises of capsular polysaccharides of *N. meningitis* A, *N. meningitis* C, *N. meningitis* Y, *N. meningitis* W135 and *N. meningitis* X formulated with *Salmonella typhi* Vi polysaccharide (ViPs) presented as lyophilized form. The bacterial capsular polysaccharides of meningitidis A, C, Y, W135 and X including Vi-Ps are presented as lyophilized pellets. The ViPs-TT vaccine antigen of the vaccine formulations according to the present invention are dissolved in normal saline or phosphate buffered saline. The diluent buffer is formulated with sodium chloride or sodium phosphate buffers. The lyophilized meningitidis A, C, Y, W135 X and ViPs formulation contains either combination of sugars selected from trehalose, sucrose and lactose as stabilizers.

A stable vaccine composition for prophylaxis against infections caused by *Neisseria meningitidis* and *Salmonella typhi* comprising: vaccine antigens, the said vaccine antigens comprising capsular polysaccharides of *Neisseria meningitidis* A, *Neisseria meningitidis* C, *Neisseria meningitidis* Y, *Neisseria meningitidis* W135, *Neisseria meningitidis* X and *Salmonella typhi* Vi capsular polysaccharide, wherein, the said composition do not contain any animal component or alcohol.

Table 14 below elucidates the various concentrations of the vaccine antigens of the vaccine formulations disclosed in the present invention.

TABLE 14

| Vaccine Formulations of the present invention | | | | | | | |
|---|---|---|---|---|---|---|---|
| | Composition in μg/0.5 ml (dose volume) | | | | | | |
| Formulation | C | Y | W135 | X | A | ViPs-TT (ViPs:TT in the ratio of 0.5 to 1.5) | Excipients |
| A1 | 50 | 50 | 50 | 50 | 50 | Not Applicable | Sodium Phosphate buffer and thiomers al, combination of sugars sucrose (up to 70% w/v), trehalose (0.5%-1% w/v) and lactose (0.5%-1% w/v). |
| A2 | 50 | 50 | 50 | 50 | 50 | 25 μg of Vi-Ps-TT conjugate | Sodium chloride buffer (normal saline) and thiomersal, combination of sugars sucrose (up to 70% w/v), trehalose (0.5%-1% w/v) and lactose (0.5%-1% w/v). |

Example 8: Biological Activity of Vaccine Formulations A1 and A2

Immunogenicity of formulations was evaluated and the results are represented in table 15.

TABLE 15

| Immunogenicity data of the vaccine formulations A1 and A2 | | | | | | | | | | | | | |
|---|---|---|---|---|---|---|---|---|---|---|---|---|---|
| Formulation | | Men A | | Men C | | Men Y | | Men W135 | | Men X | | ViPs-TT | |
| Code | Day | IgG | SBA | IgG | SBA | IgG | SBA | IgG | SBA | IgG | SBA | IgG | SBA |
| A1 | 28 | 243 | 12 | 214 | 15 | 354 | 17 | 425 | 10 | 345 | 23 | NA | NA |
| | 35 | 1169 | 32 | 7562 | 68 | 5231 | 76 | 1235 | 22 | 2314 | 79 | NA | NA |
| A2 | 28 | 215 | 11 | 254 | 12 | 156 | 16 | 254 | 12 | 165 | 24 | 2365 | 52 |
| | 35 | 1126 | 30 | 6865 | 59 | 4356 | 74 | 1254 | 25 | 2145 | 75 | 18567 | 183 |

Results—

The study performed on mice for immunogenicity indicated that all the formulations were satisfactorily immunogenic. The addition of ViPs-TT conjugate to the formulation had independent immunogenic response in the formulation and supported the concept of formulating a vaccine to target protection against meningitis and typhoid simultaneously. Thus, any of the each component individual meningococcal antigens are not impaired by the presence of other component meningococcal antigens or Vi-capsular-TT conjugate antigen, thereby conferring an antibody titer equivalent produce sufficient immune response against all the major types of meningitidis serotypes and *Salmonella typhi* infections.

Example 9: Stability of Meningococcal polysaccharides and Polysaccharide Conjugate Formulations The final vaccine formulations was reconstituted for stability studies The reconstituted vaccine antigens were pooled and incubated at 5±3° C., 37±2° C. and 56±2° C. The total polysaccharides and free polysaccharides was estimated on day zero, day 15 and $30^{th}$. The stability results are presented in table 16 and table 17.

TABLE 16

| Stability study of formulation A1. | | | | | | |
|---|---|---|---|---|---|---|
| | Stored at 5 ± 3° C. | | Stored at 37 ± 2° C. | | Stored at 56 ± 2° C. | |
| Day | Total poly-saccha-rides μg/ml | Poly-saccha-ride loss % | Total poly-saccha-ride μg/ml | Poly-saccharide loss % | Total Polyaccharide μg/ml | Total poly-saccha-ride loss % |
| Men A | | | | | | |
| 0 | 50 | <5 | 50 | <5 | 50 | <5 |
| 15 | 50 | <5 | 50 | <5 | 45 | 10 |
| 30 | 49 | <5 | 48 | <5 | 40 | 20 |
| 180 | 50 | <5 | — | — | — | — |
| 360 | 48 | <5 | — | — | — | — |
| Men C | | | | | | |
| 0 | 49 | <5 | 49 | <5 | 49 | <5 |
| 15 | 49 | <5 | 45 | 8.1 | 35 | 28.5 |
| 30 | 48 | <5 | 38 | 22.4 | 30 | 38.7 |
| 180 | 49 | <5 | — | — | — | — |
| 360 | 48 | <5 | — | — | — | — |
| Men Y | | | | | | |
| 0 | 49 | <5 | 49 | <5 | 49 | <5 |
| 15 | 48 | <5 | 44 | 10.2 | 34 | 30.6 |

TABLE 16-continued

Stability study of formulation A1.

| Day | Stored at 5 ± 3° C. Total poly-saccharides μg/ml | Poly-saccharide loss % | Stored at 37 ± 2° C. Total poly-saccharide μg/ml | Poly-saccharide loss % | Stored at 56 ± 2° C. Total Polyaccharide μg/ml | Total poly-saccharide loss % |
|---|---|---|---|---|---|---|
| 30 | 48 | <5 | 36 | 26.5 | 29 | 40.8 |
| 180 | 49 | <5 | — | — | — | — |
| 360 | 49 | <5 | — | — | — | — |
| Men W135 | | | | | | |
| 0 | 49 | <5 | 49 | <5 | 49 | <5 |
| 15 | 49 | <5 | 46 | 6.1 | 36 | 26.5 |
| 30 | 48 | <5 | 37 | 24.4 | 30 | 38.7 |
| 180 | 48 | <5 | — | — | — | — |
| 360 | 48 | <5 | — | — | — | — |
| Men X | | | | | | |
| 0 | 50 | <5 | 50 | <5 | 50 | <5 |
| 15 | 48 | <5 | 43 | 14 | 31 | 38 |
| 30 | 48 | <5 | 32 | 36 | 27 | 46 |
| 180 | 48 | <5 | — | — | — | — |
| 360 | 48 | <5 | — | — | — | — |

TABLE 17

Stability study of formulation A2

| Day | Stored at 5 ± 3° C. Total Poly-saccharide μg/ml | Poly-saccharides loss % | Stored at 37 ± 2° C. Total Poly-saccharide μg/ml | Poly-saccharide loss % | Stored at 56 ± 2° C. Total Poly-saccharide μg/ml | Poly-saccharide loss % |
|---|---|---|---|---|---|---|
| Men A Lyophilized reconstituted in formulation | | | | | | |
| 0 | 49 | <5 | 50 | <5 | 50 | <5 |
| 15 | 50 | <5 | 48 | <5 | 46 | 10 |
| 30 | 48 | <5 | 48 | <5 | 40 | 20 |
| 180 | 50 | <5 | — | — | — | — |
| 360 | 48 | <5 | — | — | — | — |
| Men C | | | | | | |
| 0 | 49 | <5 | 49 | <5 | 49 | <5 |
| 15 | 49 | <5 | 45 | 8.1 | 35 | 28.5 |
| 30 | 48 | <5 | 38 | 22.4 | 30 | 38.7 |
| 180 | 49 | <5 | — | — | — | — |
| 360 | 48 | <5 | — | — | — | — |
| Men Y | | | | | | |
| 0 | 49 | <5 | 49 | <5 | 49 | <5 |
| 15 | 48 | <5 | 44 | 10.2 | 34 | 30.6 |
| 30 | 48 | <5 | 36 | 26.5 | 29 | 40.8 |
| 180 | 49 | <5 | — | — | — | — |
| 360 | 49 | <5 | — | — | — | — |
| Men W135 | | | | | | |
| 0 | 49 | <5 | 49 | <5 | 49 | <5 |
| 15 | 49 | <5 | 46 | 6.1 | 36 | 26.5 |
| 30 | 48 | <5 | 37 | 24.4 | 30 | 38.7 |
| 180 | 48 | <5 | — | — | — | — |
| 360 | 48 | <5 | — | — | — | — |
| Men X | | | | | | |
| 0 | 50 | <5 | 50 | <5 | 50 | <5 |
| 15 | 48 | <5 | 43 | 14 | 31 | 38 |
| 30 | 48 | <5 | 32 | 36 | 27 | 46 |
| 180 | 48 | <5 | — | — | — | — |
| 360 | 48 | <5 | — | — | — | — |

TABLE 17-continued

Stability study of formulation A2

| Day | Stored at 5 ± 3° C. Total Poly-saccharide μg/ml | Poly-saccharides loss % | Stored at 37 ± 2° C. Total Poly-saccharide μg/ml | Poly-saccharide loss % | Stored at 56 ± 2° C. Total Poly-saccharide μg/ml | Poly-saccharide loss % |
|---|---|---|---|---|---|---|
| ViPs-TT | | | | | | |
| 0 | 25 | <5 | 25 | <5 | — | — |
| 15 | 25 | <5 | 25 | <5 | — | — |
| 30 | 25 | <5 | 25 | <5 | — | — |
| 180 | 24 | <5 | — | — | — | — |
| 360 | 24 | <5 | | | — | — |
| 720 | 24 | <5 | | | | |

TABLE 18

Stability study of formulation A3

| Day | Stored at 5 ± 3° C. Total Poly-saccharide μg/ml | Poly-saccharides loss % | Stored at 37 ± 2° C. Total Poly-saccharide μg/ml | Poly-saccharide loss % | Stored at 56 ± 2° C. Total Poly-saccharide μg/ml | Poly-saccharide loss % |
|---|---|---|---|---|---|---|
| Men A Lyophilized reconstituted in formulation | | | | | | |
| 0 | 50 | <5 | 50 | <5 | 50 | <5 |
| 15 | 50 | <5 | 48 | <5 | 46 | 10 |
| 30 | 48 | <5 | 48 | <5 | 40 | 20 |
| 180 | 50 | <5 | — | — | — | — |
| 360 | 48 | <5 | — | — | — | — |
| Men C | | | | | | |
| 0 | 49 | <5 | 49 | <5 | 49 | <5 |
| 15 | 49 | <5 | 45 | 8.1 | 35 | 28.5 |
| 30 | 47 | <5 | 38 | 22.4 | 30 | 38.7 |
| 180 | 49 | <5 | — | — | — | — |
| 360 | 48 | <5 | — | — | — | — |
| Men Y | | | | | | |
| 0 | 49 | <5 | 49 | <5 | 49 | <5 |
| 15 | 48 | <5 | 44 | 10.2 | 34 | 30.6 |
| 30 | 48 | <5 | 36 | 26.5 | 29 | 40.8 |
| 180 | 49 | <5 | — | — | — | — |
| 360 | 47 | <5 | — | — | — | — |
| Men W135 | | | | | | |
| 0 | 49 | <5 | 49 | <5 | 49 | <5 |
| 15 | 49 | <5 | 46 | 6.1 | 36 | 26.5 |
| 30 | 49 | <5 | 37 | 24.4 | 30 | 38.7 |
| 180 | 48 | <5 | — | — | — | — |
| 360 | 48 | <5 | — | — | — | — |
| Men X | | | | | | |
| 0 | 50 | <5 | 50 | <5 | 50 | <5 |
| 15 | 48 | <5 | 43 | 14 | 31 | 38 |
| 30 | 48 | <5 | 32 | 36 | 27 | 46 |
| 180 | 48 | <5 | — | — | — | — |
| 360 | 47 | <5 | — | — | — | — |
| Vi-Ps | | | | | | |
| 0 | 25 | <5 | 25 | <5 | — | — |
| 15 | 24 | <5 | 25 | <5 | — | — |
| 30 | 25 | <5 | 25 | <5 | — | — |
| 180 | 25 | <5 | — | — | — | — |
| 360 | 24 | <5 | | | — | — |

Results:

Formulation A1 has been found to be stable over the period of 360 days when stored at 5° C. However 20% loss in lyophilized Meningococcal A polysaccharide has been observed. Over all the complete reconstituted formulation was found stable at 5° C. up to 360 days of study period. Formulation A2, and A3 was also found to be stable 5° C. up to 360 days of study period.

We claim:

1. A vaccine composition comprising:
   - isolated capsular polysaccharide of each of *Neisseria meningitidis* A, *Neisseria meningitidis* C, *Neisseria meningitidis* Y, *Neisseria meningitidis* W135, and *Neisseria meningitidis* X;
   - a capsular polysaccharide of *Salmonella typhi* Vi (ViPs) conjugated to tetanus toxoid (TT), wherein the ratio of ViPs to TT in the conjugate is 0.5:1.5;
   - a combination of sugars selected from sucrose, trehalose, lactose, maltose and glucose; and
   - a buffer selected from normal saline and phosphate buffer saline, wherein the composition contains no animal components and no alcohol.

2. The vaccine composition of claim 1, wherein the capsular polysaccharide of each of *Neisseria meningitidis* A, *Neisseria meningitidis* C, *Neisseria meningitidis* Y, *Neisseria meningitidis* W135, and *Neisseria meningitidis* X is present at a concentration of 50 micrograms per 0.5 ml.

3. The vaccine composition of claim 1, wherein the Vi-TT conjugate is present at a concentration of 25 micrograms per 0.5 ml.

4. The vaccine composition of claim 1 further comprising an adjuvant.

5. The vaccine composition of claim 1, wherein said combination of sugars is up to 70% w/v sucrose, 0.5% to 1% trehalose and 0.5% to 1% w/v lactose.

6. The vaccine composition of claim 1, further comprising a preservative.

7. The vaccine composition of claim 6, wherein the preservative is thimerosal.

8. The vaccine composition of claim 1, wherein the capsular polysaccharides of the *Neisseria meningitidis* A, *Neisseria meningitidis* C, *Neisseria meningitidis* Y, *Neisseria meningitidis* W135, and *Neisseria meningitidis* X are obtained by using culture media through a two-shot feeding strategy and continuous feeding using a feed media composition.

9. The vaccine composition of claim 8, wherein the culture media are yeast extract-based culture media, soy peptone-based culture media, or vegetable infusion protein-based culture media.

10. The vaccine composition of claim 9, wherein the yeast extract-based culture media comprises 0.1-2.0 gm/mL of ammonium chloride, 5-20 gm/mL of glutamic acid, 0.25 to 0.4 gm/mL of serine, 0.25 to 0.4 gm/mL of arginine, 0.2 to 0.3 gm/mL of L-cysteine, 4 gm/mL of dipotassium hydrogen phosphate, 5 gm/mL of sodium chloride, 0.73 gm/mL of magnesium sulphate, 0.030 gm/mL of calcium chloride, 0.04 gm/mL of ferrous citrate, 5-20 gm/mL of yeast extract, and 10-20 gm/mL of glucose.

11. The vaccine composition of claim 9, wherein the soy peptone-based culture media comprises 0.1-2.0 gm/mL of ammonium chloride, 5-20 gm/mL of glutamic acid, 0.25 to 0.4 gm/mL of serine, 0.25 to 0.4 gm/mL of arginine, 0.2 to 0.3 gm/mL of L-cysteine, 4 gm/mL of dipotassium hydrogen phosphate, 5 gm/mL of sodium chloride, 0.73 gm/mL of magnesium sulphate, 0.030 gm/mL of calcium chloride, 0.04 gm/mL of ferrous citrate, 10 mg/mL of soy peptone, and 10 gm/mL of glucose.

12. The vaccine composition of claim 9, wherein the vegetable infusion protein-based culture media comprises 0.1-2.0 gm/mL of ammonium chloride, 5-20 gm/mL of glutamic acid, 0.25 to 0.4 gm/mL of serine, 0.25 to 0.4 gm/mL of arginine, 0.2 to 0.3 gm/mL of L-cysteine, 4 gm/mL of dipotassium hydrogen phosphate, 5 gm/mL of sodium chloride, 0.73 gm/mL of magnesium sulphate, 0.030 gm/mL of calcium chloride, 0.04 gm/mL of ferrous citrate, 10 mg/mL of 30 k diafiltered vegetable infusion peptone, and 10 gm/mL of glucose.

13. The vaccine composition of claim 7, wherein the feed media composition comprises 0.5-50% of sucrose, 0.0005-0.02 gm/L of cationic peptide LL37, 10-50 gm/L of sodium glutamate, 0-10 gm/L arginine, 0-10 gm/L serine, 0-5 gm/L of L-cysteine, 2 gm/L of magnesium chloride and 0.04 gm/L of ferrous citrate.

14. The vaccine composition of claim 7, wherein the two-shot feeding strategy is carried out by injecting the feed media composition at $4^{th}$ hour and $6^{th}$ hour during fed-batch mode fermentation.

15. The vaccine composition of claim 7, wherein the feed media composition for the two-shot feeding strategy comprises:
   - a first shot comprising 0.5-50% of sucrose, 0.0005-0.02 gm/L of cationic peptide LL37, 10-50 gm/L of sodium glutamate, 0-10 gm/L arginine, 0-10 gm/L serine, 0-5 gm/L of L-cysteine, 2 gm/L of magnesium chloride and 0.04 gm/L of ferrous citrate; and
   - a second shot comprising 0.5-50% w/v of sucrose, 0.0005-0.02 gm/L of cationic peptide LL37, 0-60 gm/L of sodium glutamate, and 2-4 gm/L magnesium chloride.

16. The vaccine composition of claim 1, wherein the capsular polysaccharides of the *Neisseria meningitidis* A, *Neisseria meningitidis* C, *Neisseria meningitidis* Y, *Neisseria meningitidis* W135, and *Neisseria meningitidis* X are purified.

17. The vaccine composition of claim 16, wherein the capsular polysaccharides are purified without using ethanol.

18. The vaccine composition of claim 16, wherein the capsular polysaccharides are purified by precipitation with zinc acetate at a concentration of 0.5 to 5% w/v or 1.8 to 2.5% w/v.

19. The vaccine composition of claim 16, wherein the capsular polysaccharides are purified by precipitation with 0.5 to 1M sodium citrate.

20. The vaccine composition of claim 16, wherein the capsular polysaccharides are purified by at least one of simultaneous anion and cation exchange Ceramic Hydroxy Apatite Raisin chromatography, ion-exchange chromatography, gel filtration chromatography, hydrophobic column chromatography, and fractionation with a salt or an organic solvent.

* * * * *